(12) United States Patent
Castor et al.

(10) Patent No.: US 6,465,168 B1
(45) Date of Patent: *Oct. 15, 2002

(54) METHODS AND APPARATUS FOR THE INACTIVATION OF VIRUSES

(76) Inventors: Trevor P. Castor, 216 Sylvia St., Arlington, MA (US) 02174; Arthur D. Lander, 1850 Glenneyre St., Laguna Beach, CA (US) 92651

( * ) Notice: Subject to any disclaimer, the term of this patent is extended or adjusted under 35 U.S.C. 154(b) by 0 days.

This patent is subject to a terminal disclaimer.

(21) Appl. No.: 09/474,475

(22) Filed: Dec. 29, 1999

Related U.S. Application Data

(63) Continuation-in-part of application No. 07/844,513, filed on Mar. 2, 1992, now abandoned.

(51) Int. Cl.[7] ............................. A01N 1/02; C12N 7/06; C12M 1/36

(52) U.S. Cl. ......................... 435/2; 435/238; 435/286.1; 435/286.6

(58) Field of Search ....................... 435/238, 2, 286.1, 435/286.6

(56) References Cited

U.S. PATENT DOCUMENTS 4,749,522 A * 6/1988 Kamarei
5,877,005 A * 3/1999 Castor et al.

* cited by examiner

*Primary Examiner*—Christopher R. Tate
*Assistant Examiner*—Michele C. Flood

(57) ABSTRACT

The present invention is directed to methods and apparatus for inactivating viruses associated or potentially associated with blood derived samples. The process and apparatus feature critical, supercritical or near critical fluids.

12 Claims, 1 Drawing Sheet

METHODS AND APPARATUS FOR THE INACTIVATION OF VIRUSES

This application is a continuation in part of U.S. Ser. No. 07/844,513 filed Mar. 2, 1992 now abandoned.

BACKGROUND OF THE INVENTION

Infectious viruses can be readily transmitted via products derived from biological sources or instruments used in medical procedures. By way of example, viruses may be transmitted via products and materials derived from blood products. Surgical instruments, which instruments are not adequately disinfected, have long been recognized as a means of viral transmission.

Viruses commonly associated with infection from products derived from blood products include hepatitis B virus (HBV), as well as non-A and non-B hepatitis (NANBHV), and the human immuno-deficiency virus, associated with human immuno-deficiency syndrome (AIDS). Products derived from blood pose special problems. Methods and compositions commonly used to disinfect materials tend to denature proteins, rendering the product useless. There is a need for methods and compositions that inactivate viruses in products and materials derived from biological materials and materials intended for human use.

A virion is an individual infectious particle or agent. The term "virus" is used to denote a group of individual virions having common features in the nature of a species. The term "viruses" is used to denote more than one species.

As used herein, the term "inactivate" with respect to viruses means rendering one or more individual virions unable to infect its normal host cell or replicate in its normal host cell. The term specifically excludes the removal or isolation of one or more virions from the materials in which it is found. Indeed, in accordance with the present invention, the constituents of the virion may remain in the materials in which the virion is present. As used herein, the term "constituents" refers to the proteins, peptides, fats and waxes, and nucleic acid which comprise the virion particle. Viral activity or inactivity is usually measured by testing for the development of colonies in a suitable host culture. The development of plaques of dead cells indicates the presence of the virus and its ability to infect host cells and replicate.

As used herein, the term "sample" refers to the materials that need to be processed to reduce the number of virions. The sample may be materials derived from biological materials, such as, by way of example, blood products, tissues, cell cultures and the like. Or, in the alternative, the sample may be a instrument or implement for which the presence of virions may pose a danger or problem. By way of example, surgical and or dental implements and instruments require disinfection prior to use.

Certain aspects of the present invention employ materials known as supercritical, critical and near critical fluids. A gas becomes a critical fluid at its critical temperature and at its critical pressure. A gas becomes a supercritical fluid at conditions which equal or exceed both its critical temperature and critical pressure. The critical temperature and critical pressure are intrinsic thermodynamic properties of all sufficiently stable pure compounds and mixtures. Carbon dioxide, for example, becomes a supercritical fluid at conditions which equal or exceed its critical temperature of 31.1.° C. and its critical pressure of 72.8 atm (1,070 psig). In the supercritical fluid region, normally gaseous substances, such as carbon dioxide, become dense phase fluids which have been observed to exhibit greatly enhanced solvating power. At a pressure of 204 atm (3000 psig) and a temperature of 40° C., carbon dioxide has a density of approximately 0.8 g/cc and behaves much like a nonpolar organic solvent having a dipole moment of zero debyes.

A supercritical fluid displays a wide spectrum of solvating properties as its density is strongly dependent upon temperature and pressure. Temperature changes of tens of degrees or pressure changes by tens of atmospheres can change a compound's solubility in a supercritical fluid by an order of magnitude or more. This feature allows for the fine tuning of solvation and the fractionation of mixed solutes.

The selectivity of non-polar supercritical fluid solvents can be enhanced by the addition of compounds known as modifiers (also known as entrainers and cosolvents). These modifiers are typically somewhat polar organic solvents such as acetone, ethanol. methanol, methylene chloride or ethyl acetate. Varying the proportion of modifier allows a wide latitude in the variation of solvent power.

Supercritical fluids exhibit liquid-like density yet retain gas-like properties of high diffusivity and low viscosity. The latter increases mass transfer rates, significantly reducing processing times. Supercritical fluids exhibit low surface tension allowing facile penetration into micro-porous materials.

A material at conditions that border its supercritical state will have properties that are similar to those of the substance in the supercritical state. A material at conditions that border its supercritical state are known as "near critical fluids." For the purposes of this application, a near critical fluid is a fluid that is:

(a) at a temperature between its critical temperature ($T_c$) and 75% of its critical temperature and at a pressure at least 75% of its critical pressure ($P_c$); or, (b) at a pressure between its critical pressure ($P_c$) and 75% of its critical pressure and a temperature at least 75% of its critical temperature (measured in absolute scales of degrees Kelvin and psia).

Table 1 below sets forth physical properties of materials commonly employed as supercritical, critical or near critical fluids. To simplify the terminology, individuals skilled in the art will refer to materials which are at conditions which are supercritical or near critical as critical fluids, as "critical fluids." This application will refer to supercritical, near critical or critical fluids collectively as "SCNCorC" fluids.

TABLE 1

Physical properties of critical fluid solvents

| Fluid | Formula | BP, | $P_{vap}$, | $T_c$, | $P_c$ | 0.75 $T_c$, | 0.75 $P_c$ |
|---|---|---|---|---|---|---|---|
| Carbon Dioxide | $CO_2$ | −78.5 | 860 | 31.1 | 1070 | −45.0 | 803 |
| Nitrous Oxide | $N_2O$ | −88.5 | 700 | 36.5 | 1051 | −41.0 | 788 |
| Propane | $C_3H_8$ | −42.1 | 130 | 96.7 | 616 | 4.2 | 462 |
| Ethane | $C_2H_6$ | −88.7 | 570 | 32.3 | 709 | −44.1 | 531 |
| Ethylene | $C_2H_4$ | −103.8 | NA | 9.3 | 731 | −61.4 | 548 |
| Freon 11 | $CCl_3F$ | 23.8 | 15 | 198.1 | 639 | 80.3 | 480 |
| Freon 21 | $CHCl_2F$ | 8.9 | 24 | 178.5 | 750 | 65.6 | 562 |
| Freon 22 | $CHClF_2$ | −40.8 | 140 | 96.1 | 722 | 3.8 | 541 |
| Freon 23 | $CHF_3$ | −82.2 | 630 | 26.1 | 700 | −48.7 | 525 |

As used above, temperature is expressed in degrees Centigrade, and pressure is expressed in psig at 25° C. As used above BP represents normal boiling point, and $P_{VAP}$ represents vapor pressure.

There exists a need to render viruses, especially enveloped and lipid coated viruses in proteinaceous products, inactive without incurring substantial denaturation. In particular, there exists a need to render viruses inactive in blood derived products without changing the nature of the blood products necessary for their function.

SUMMARY OF THE INVENTION

The present invention relates to methods and apparatus for inactivating viruses associated with a sample. One embodiment of the present method relates to blood derived samples, such as plasma, serum, blood fractions, platelets and the like. The method comprises the steps of forming an admixture of a blood derived sample with a critical, near critical or supercritical fluid which critical, near critical or supercritical fluid is capable of being received by one or more virions associated with the sample. Upon removal of the critical, near critical, or supercritical fluid one or more virions are inactivated. The method further comprises the step of removing the critical, near critical or supercritical fluid to render one or more virions inactive while retaining the constituents of the virus to form a processed blood derived product. The processed blood derived product exhibits a reduction of viral activity compared with the original blood derived sample The steps of the process can be repeated to effect a desired level of inactivation of virions.

The present method has particular application for the inactivation of virus associated with blood borne illnesses, such as AIDS, in blood derived samples. Surprisingly and unexpectedly, under conditions that leave the blood derived sample substantially unchanged, a four log reduction in viral activity can be achieved. As used herein, when referring to blood derived products, the term "substantially unchanged" means exhibiting negligible denaturation of blood proteins to no more than fifty percent reduction in the activity of blood proteins. The time in which the blood derived sample may be processed to achieve this four log reduction in viral activity may be as little as five minutes.

Preferably, the critical, supercritical or near critical fluid is at a temperature in the range of 0° C. to 100° C. This temperature range is in a range in which proteins held in aqueous solutions do not denature. Preferably, the critical, supercritical or near critical fluid has a temperature that does not exceed 60° C. And even more preferred, the critical, super critical or near critical fluid has a range of 4° C. to 40° C.

Preferably, the critical, supercritical or near critical fluid has a pressure in which the admixture is made and maintained which pressure is 0.75 to 20.0 times the critical pressure of the gas comprising such fluid.

A preferred fluid is selected from one or more of the gases of the group consisting of fluorocarbons, such as chlorofluoromethanes, alkanes, such as ethylene, propane and ethane, and binary gases such as nitrous oxide and carbon dioxide. Preferably, the critical, supercritical or near critical fluid further comprises one or more modifiers selected from the group consisting of ethanol, methanol, acetone, and ethylene glycol.

A particularly preferred critical, supercritical or near critical fluid is nitrous oxide at approximately 12° C. to 30° C. at 800 to 1600 psig; and, even more preferred, nitrous oxide at approximately 16° C. to 26° C. at 1000 to 1400 psig; and, most preferred, nitrous oxide at approximately 21° C. at approximately 1200 psig. At these conditions, blood proteins show little change in function.

A particularly preferred critical, supercritical or near critical fluid is chlorodifluoromethane at approximately 10° C. to 60° C. at 1000 to 4000 psig; and, even more preferred, chlorodifluoromethane at approximately 40° C. at 2000 to 4000 psig.

One embodiment of the present invention features an apparatus for inactivating one or more virions in a blood sample. The apparatus comprises a vessel for forming an admixture of a blood derived sample with a critical, near critical or supercritical fluid which critical, near critical or supercritical fluid is capable of being received by one or more virions associated with the sample. Upon removal of the critical, near critical, or supercritical fluid one or more virions are inactivated. The apparatus further comprises depressurization means for removing the critical, near critical or supercritical fluid to render one or more virions inactive while retaining the constituents of the virus in the sample.

Preferably, the vessel is in communication with a continuous supply of the blood sample. And, the depressurization means is capable of receiving a continuous supply of the admixture of the blood sample and the critical, supercritical or near critical fluid.

Preferably, the vessel retains the admixture for a period of time to effect a thousand-fold to four thousand-fold reduction of active virions. And, more preferably, the vessel retains the admixture for a period of five to thirty minutes.

These and other benefits of the present invention will be apparent to individuals skilled in the art upon reading the detailed description and viewing the drawings.

DETAILED DESCRIPTION

Figure 1:
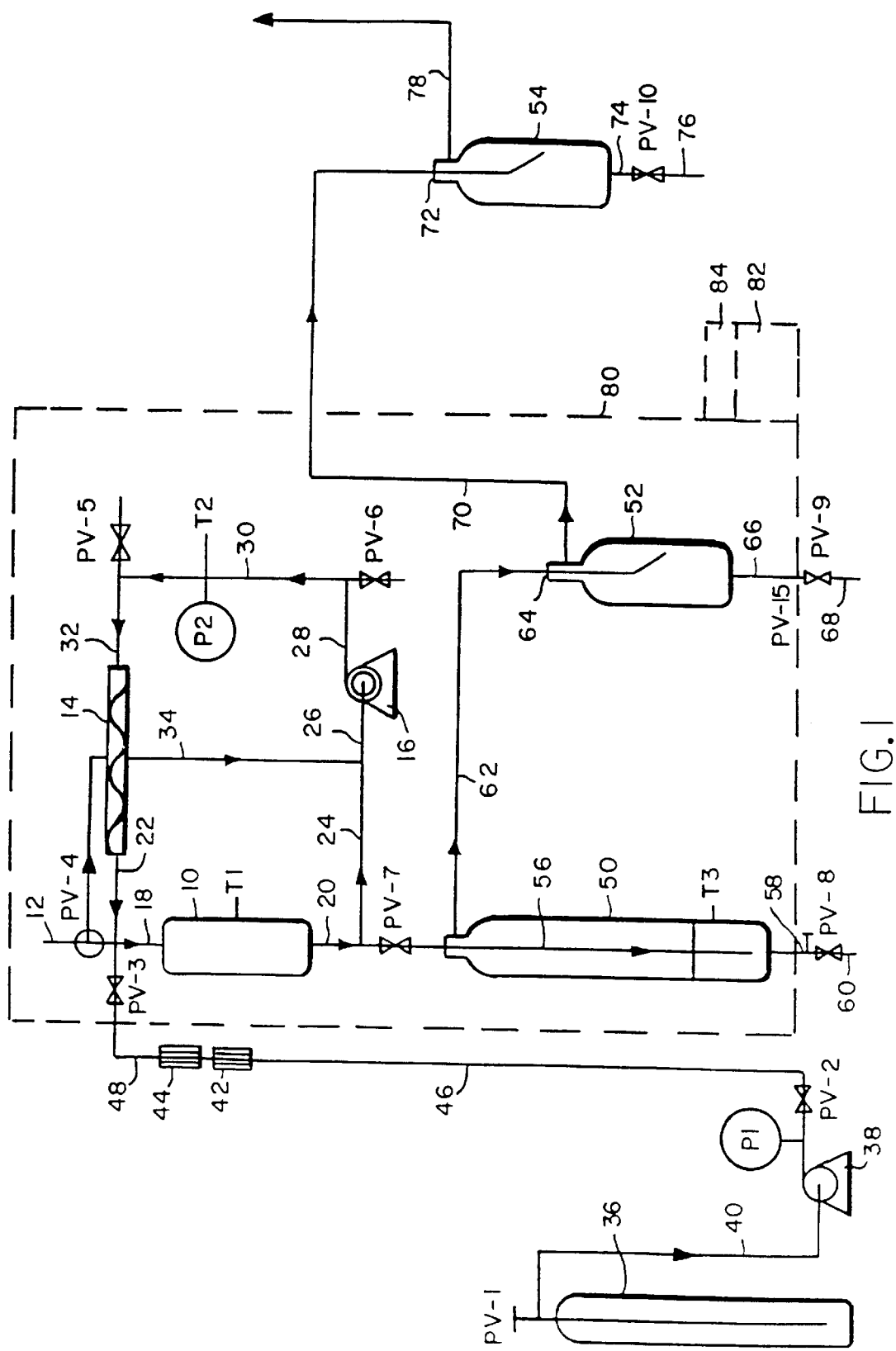
FIG. 1 is a schematic illustration of an apparatus according to the invention.

The present invention will be described in detail as a method and apparatus for inactivating one or more virions associated with a blood derived sample. Individuals skilled in the art will readily recognize the application of the methods and apparatus of the present invention to other purposes. And, individuals skilled in the art will recognize the possibility of changes and modifications to the present apparatus. This description is only exemplary and is not to be interpreted as limiting.

Embodiment of the present method relate to blood derived samples. As used herein, blood derived samples refer to plasma, serum, blood plasma fractions, platelets and synthetic blood or blood-like materials.

Generally, the method comprises the steps of forming an admixture of a blood derived sample with a critical, near critical or supercritical fluid which critical, near critical or supercritical fluid is capable of being received by one or more virions associated with the sample. Upon removal of the critical, near critical, or supercritical fluid one or more virions are inactivated. The method further comprises the step of removing the critical, near critical or supercritical fluid to render one or more virions inactive while retaining the constituents of the virus in the sample. This method will be described more fully with respect to the apparatus which description follows.

One embodiment of the present invention features an apparatus for inactivating one or more virions in a blood sample. The apparatus comprises a vessel for forming an admixture of a blood derived sample with a critical, near critical or supercritical fluid which critical, near critical or supercritical fluid is capable of being received by one or more virions associated with the sample. Upon removal of the critical, near critical, or supercritical fluid one or more virions are inactivated. The apparatus further comprises depressurization means for removing the critical, near critical or supercritical fluid to render one or more virions inactive while retaining the constituents of the virus in the sample.

Preferably, the vessel is in communication with a continuous supply of the blood sample. And, the depressurization means is capable of receiving a continuous supply of the admixture of the blood sample and the critical, supercritical or near critical fluid.

Preferably, the vessel retains the admixture for a period of time to effect a thousand fold to four thousand fold reduction of active virions. And, more preferably, the vessel retains the admixture for a period of five to thirty minutes. An apparatus for performing the present method and incorporating features of the present invention is described in FIG. 1.

The apparatus includes a source of fluid, a high-pressure, recirculation loop, a separation chamber, and at least one low pressure trap. Viral inactivation occurs in the high-pressure recirculation loop, which is rated for continuous operation at 5,000 psig and 100° C. The high-pressure recirculation loop consists of: a chamber 10 into which the material to be treated and the critical fluid are introduced; an injection port 12 for introducing the product into the soaking chamber; a static in-line mixer 14 for continously mixing the mixture of product and fluid; and a circulation pump 16 for moving the mixture to the in-line mixer 14; two thermocouples, one associated with the separation chamber (thermocouple T1) and the other located just upstream of the static in-line mixer; and various interconnecting lines 18, 20, 22, 24, 26, 28, 30, 32, 34 and 36 as well as several process valves PV-3, PV-4, PV-5, PV-6 and PV-7 for channeling and controlling the movement of fluid throughout the high-pressure recirculation loop.

Critical fluid viral inactivation of a proteinaceous product containing viral contaminants can be conducted in an apparatus such as the one shown in FIG. 1, or in other variations of the same adapted to permit a critical fluid to be added to a product, adapted to control pressure, temperature, mixing and residence time, and adapted to separate the critical fluid from the virally inactivated proteinaceous product.

Process valves PV-3, PV-5, PV-6 and PV-7 are all ¼" full-opening two-way Stainless Steel ball valves rated for 6,000 psig at 100 C. (Parker, Huntsville, Ala. A); PV-4 is a three-way stainless steel ball valve (Parker, Huntsville, Ala.). In some embodiments of the invention, process valve PV-7 is a back-pressure regulator (Model No. 26-1722-24, Tescom Corporation, Elk River, Minn.) with which the operator can control the decompression of the separation chamber and the high pressure circulation loop. Soaking chamber 10 is a high pressure stainless steel vessel having a capacity of 150 ml and an operating pressure of 5,000 psig at 100 C. (Model Z148, Hoke Inc., Cresskill, N.J.). A K-type thermocouple T1 is placed in contact with the outer surface of the soaking chamber 10 and the temperature is monitored on a digital temperature-indicator-controller (Model No. CN-310KC, Omega Engineering, Inc., Stamford, Conn.).

Soaking chamber 10 has a top inlet line 18 and a bottom outlet line 20. The inlet line 18 communicates at a fluid joint with the source of critical fluid, the product injection port 12, and the outlet line 22 of the static in-line mixer 14. The outlet line 20 of the soaking chamber 10 and one end of conduit line 24 are connected at a fluid joint which joint in turn is connected to the decompression valve PV-7. The other end of conduit line 24 is connected at a fluid joint to the inlet line 26 of the circulation pump 16. The particular circulation pump 16 used was variable speed (0 to 9,000 rpm), high pressure (5,000 psig at 150 C.) gear pump capable of a flow rate of 300 ml/min at a pressure differential of 10 to 20 psig (Modified Model No. 183, custom-built by Micropump, Concord, Calif.). The circulation pump 16 had a cooling head made of an aluminum block connected to a circulating, refrigerated water bath capable of maintaining temperatures as low as 5 C. and a cooling rate 15,300 Btu/h (Model No. HX-150, Neslab, Inc., Concord, N.H.). The discharge line 28 of circulation pump 16 is connected at a fluid joint to one end of the conduit line 30, which joint in turn is connected to drain valve PV-6. The other end of conduit line 30 is connected at a fluid joint to the inlet line 32 of the static in-line mixer 14 which joint in turn is connected to vent valve PV-5. Conduit 30 has an in-line pressure indicator P-2 and an in-line K-type thermocouple T2 which is connected to a temperature-indicator controller (Model No. CN-310KC, Omega, Stamford, Conn.).

Static in-line mixer 14 is a 3/16 "ID×7½" long ×27 element tube mixer rated for 4,642 psig at 300 F. (Kenics Mixer Model No. 37-03-075, Chemineer, Dayton, Ohio). The outlet line 22 of the static in-line mixer 14 and the inlet line 18 to the separation chamber 10 are connected at a fluid joint. This joint is connected to critical fluid feed valve PV-3 and also is connected to the three-way process valve PV-4. The three-way process valve PV-4 allows fluid connection between the injection port 12 and either the recycle conduit 34 or the inlet line 18 of the soaking chamber 10. The recycle conduit at its other end is connected to the joint between the conduit line 24 and inlet 26 of the circulation pump 16.

The critical fluid is in fluid communication with feed valve PV-3 via a series of conduit lines interrupted by valves, pumps and filters. Release of critical fluid from the container 36 is controlled by valve PV-1 on the head of the high pressure container. The fluid is conducted from the container 36 to the inlet of compressor 38 via conduit line 40. The particular compressor employed was a single-ended diaphragm compressor which can compress gas or liquid up to 10,000 psig at a flow rate of 40 standard liters per minute (Model No. J-46-13411, Superpressure Gas Compressor, Newport Scientific, Jessup, Md.). A process valve PV-2 is connected to the outlet of the compressor 38 and can be closed when the desired pressure is achieved. The fluid is conducted from the compressor 38 to a pair of in-line filters 42, 44 via conduit line 46. The particular in-line filters used were a 7 micron sintered stainless steel cup filter 42 (Model No. SS-8F-K4-7 in a 6TF stainless steel housing, Nupro Company, Willoughby, Ohio) and a 0.5 micron sintered stainless steel cup filter 44 (Model No. SS-8F-K4-05 in a 6TF stainless steel housing, Nupro Company, Willoughby, Ohio). The fluid exits the outlet of filter 44 and is conducted via conduit 48 to valve PV-3.

The high pressure recirculation loop interfaces with the product recovery, low pressure half of the apparatus which is made up of a 500 ml decompression chamber 50, a first low pressure trap 52, and several two-way valves and connecting lines. The exhaust system consists of a second low pressure trap 54 leading to a vent line which exhausts to the atmosphere. In other embodiments of this invention, the vented critical fluid is first filtered and then recycled to the inlet of the compressor P-1.

The mixture in the soaking chamber 10 can be moved through the outlet line 20 via decompression valve PV-7 to a decompression tube 56 which extends to within about ¼" of the bottom of decompression chamber 50. The decompression chamber 50 has one inlet through which decompression tube 56 is inserted and sealed, and two outlet lines.

The bottom outlet line 58 exits the bottom of the chamber 50 and is connected to process valve PV-8 (same type as PV-2) which in turn is connected to a sample port 60 for the recovery of liquid solvents and slurries. The top outlet line 62 exits the top of the decompression chamber 50 and is connected to low pressure trap 52. The particular decompression chamber employed was a 500 ml stainless steel high pressure chamber rated fro 5,000 psig at 100 C. (Model No. Z152, Hoke Inc., Cresskill, N.J.).

Low pressure trap 52 has one inlet 64 through which the top outlet line 62 of the decompression chamber 50 is inserted and sealed. It also has two outlet lines. The bottom outlet line 66 exits the bottom of the low pressure trap 52 and is connected to process valve PV-9 which in turn is connected to a sample port 68 for the recovery of any liquid solvents and slurries carried over during the decompression process. The top outlet line 70 exits the top of low pressure trap 52 and is connected to a second low pressure trap 54. The second low pressure trap 54 has one inlet 72 through which the top outlet line 70 of low pressure trap 52 is inserted and sealed and two outlet lines. The bottom outlet line 74 exits the bottom of the second low pressure trap 54 and is connected to process valve PV-10 which is connected to a sample port 76 for the recovery of any liquid solvents and slurries carried over during the decompression process. The top outlet line 78 exits the top of second low pressure trap 54 and is vented to atmosphere. Low pressure traps 52 and 54 are 150 ml high pressure Monel chambers rated for 5,000 psig at 100 C. (Model No. Z152, Hoke Inc., Cresskill, N.J.).

For reasons of safety and equipment flexibility, the product recovery half of the apparatus is designed for continuous operation at a pressure of 5,000 psig at 100 C. Both the high pressure circulation loop and the product recovery half of the apparatus are enclosed in a polycarbonate (Lexan) box 80 which serves as a containment chamber. This chamber is heated by a 1500 W (Pelonis) heater 82 and controlled by a solid state ON-OFF temperature-indicator-controller 84 (Model No. CN-310KC, Omega, Stamford, Conn.) based on the in-line temperature T2 in conduit 30 attached to the discharge line 28 of the circulation pump P-2 16.

As an initial condition, the system is cleaned, sterilized and dried, and is at operating temperature (room temperature to 40 C.) with all process valves (PV) in the closed position.

To accomplish this, the system was rinsed with 0.5mM EDTA in order to complex and remove any metal traces on the inside of the apparatus. The system is sterilized by filling with 70% ethanol solution via the 7 micron and the 0.5 micron filter elements. They system was then heated to 40 C. and the ethanol circulated in the high pressure circulation loop of the apparatus for about 30 minutes. The blowdown valve PV-7 is then opened and the entire system filled with 70% ethanol to the vent valve after LPT-2. All valves, namely PV-4, PV-5, PV6, PV-8, PV-9 and PV-10, are bled until ethanol is seen. Valves PV-4 and PV-6 were covered with gauze soaked in 70% ethanol and then covered with aluminum foil. The system was held at 40 C. for approximately 30 minutes. The ethanol is then displaced from the system with pressurized (around 100 psig) and filtered (through the 7 micron and 0.5 micron filters) nitrogen through valves PV6, PV-8, PV-9 and PV-10. When liquid is no longer coming out, these valves are all covered with ethanol soaked gauze and aluminum foil. The entire system is then rinsed with 0.2 micron filtered distilled and deionized (DDI) water. All valves are bled and the water displaced out of the system using filtered nitrogen under pressure. The sample loading tube, collection flasks and the fill bell (with silicon tubing attached) are all sterilized in an autoclave set at 250° F. for 30 minutes on fast exhaust. The loading tube was wrapped in gauze; about 2 ml of DDI water (in order to generate steam) was placed in the flasks which had a gauze and cotton plug covered with aluminum foil. When the steam cycle was completed, a 20 minute drying cycle was conducted.

In its normal operating mode, valves PV-4 and PV-5 are opened and an aliquot of test solution is aseptically introduced through the 3-way valve PV-4 using a sterile syringe and a presterilized loading tube. The 3-way valve PV-4 is then turned so that the critical fluid recycle line communicates with the soaking chamber, and the vent valve PV-5 is closed. PV-1 is then opened, supplying the solvent to the compressor P-1. The compressor is turned on and immediately thereafter valves PV-2 and PV-3 are opened, introducing the critical fluid solvent into the high pressure circulation loop. When operating pressure is attained, the compressor is turned off and valve PV-3 is closed.

After system stabilization, the circulation pump P-2 is turned on and its speed adjusted, typically to 75% of maximum speed or 6,750 rpm. P-2 draws both the proteinaceous product from the bottom of the soaking chamber and the critical fluid phase from the top of the same unit. The mixture is then pumped counter-clockwise, mixed by static in-line mixer and returned to the soaking chamber. After mixing for a defined residence time, P-2 is turned off. The decompression valve PV-7 is then fully opened to depressurize the soaking chamber and the high pressure circulation loop. The rate of decompression was approximately 500 psig per second when PV-7 is a ¼" ball valve. By using a back-pressure regulator instead of a ¼" ball valve as the decompression valve PV-7, the rate of decompression can be controlled. In some experiments, the rate of decompression was controlled to approximately 2,000 psig per minute. No differences were observed between rapid (500 psig per second) and slow (1,000 psig per minute) rates of decompression on the impact of critical fluid on viral infectivity and product activity.

The experiments in Example 1 below were conducted with slow decompression while the experiments in the remaining examples presented below were conducted with rapid decompression. After decompression, product was aseptically collected into a sterile flask from the decompression chamber 50 through sample port 60 which was aseptically connected to a sterile fill bell. The collected sample was stored on ice until assayed.

The critical, supercritical or near critical fluid is, preferably, at a temperature in the range of 0° C. to 100° C. This temperature range is in a range in which proteins held in aqueous solutions do not denature. Preferably, the critical, supercritical or near critical fluid has a temperature that does not exceed 60° C. And even mor preferred, the critical, super critical or near critical fluid has a range of 4° C. to 40° C.

Preferably, the critical, supercritical or near critical fluid has a pressure in which the admixture is made and maintained which pressure is 0.75 to 20.0 times the critical pressure of the gas comprising such fluid.

A preferred fluid is selected from one or more of the gases of the group consisting of fluorocarbons, such as chlorofluoromethanes, alkanes, such as ethylene, propane and ethane, and binary gases such as nitrous oxide and carbon dioxide. Preferably, the critical, supercritical or near critical fluid further comprises one or more modifiers selected from the group consisting of ethanol, methanol, acetone, and ethylene glycol In the examples described herein, samples of a recombinant murine C-type retrovirus were prepared as follows. The cell line Psi-2 (Mann et al., 1983, Cell 33: 153–159), which produces defective Moloney murine leukemia virus particles (particles that lack viral nucleic acid, but are otherwise wild type), was transfected with plasmid DNA consisting of the retrovirus vector LNCX (Miller and Rosman, 1989, Biotechniques 7:980–990) that had previously been modified by the insertion of a chimeric beta-tubulin gene (Bond et al., 1986, Cell 44:461–468) into the Stu 1 site of the LNCX vector. Clonal cell lines stably expressing the transfected DNA were derived and maintained as virus-producing stocks. By packaging the RNA produced by the transfected DNA into the defective particles, these cells produce infectious particles that are entirely normal with respect to overall structure, stability, and mode of infection, but containing the plasmid-derived rather that the wild type, genetic material (Mann et al., Ibid).

Because the LNCX sequences contain the antibiotic resistance gene neo and a suitable promoter, infection of cells with the recombinant retrovirus confers upon the cells resistance to the antibiotic Geneticin (G418). Conferral of Geneticin-resistance onto cells and their progeny was therefore used as the property by which virus titers were determined. Specifically, virus stocks were prepared by culturing the virus-producing cells at high density (50% confluence) in fresh culture medium (Dulebecco's modified Eagle's medium supplemented with 10% iron-supplemented calf serum [Hyclone, Inc., Logan, UT], glutamine [1 mM], penicillin [100 U/ml] and streptomycin [100 $\mu$g/ml] for 18 hours at 37 C. in a humidified 5% CO2 atmosphere. Culture medium was harvested and passed through a 0.2 micron filter, divided into aliquots, quick frozen using a dry-ice/ethanol bath and stored at −80° C. Immediately before use, samples were warmed in a 37 C. water bath until just thawed and held on ice. Aliquots of a single virus preparation were used for the examples described below.

After virus-containing samples were mixed with other materials and treated as described in each of the examples, they were returned to ice, and assayed within 8 hours. Titer tests were performed by seeding 35 mm-style culture dishes with a mouse fibroblast line (NIH3T3 cells) in 3 ml of the culture medium described above at a density of 10,000 cells per well the evening before the assay was to be performed. Virus samples were added to the culture medium over the cells at various dilution from $10^0$ (undiluted) to $10^{-6}$. In some cases (where indicated), polybrene (Aldrich Chemical Co.) was added along with virus at a final concentration of 2 $\mu$g/ml. Polybrene is a polycation that enhances the infectivity of retroviruses up to 100-fold, apparently by enhancing the adsorption of viral particles to cell surfaces; polybrene is commonly used in assaying mouse retrovirus titers. After addition of virus, test cells were returned to the incubator overnight, and then washed into fresh medium containing 1 mg/ml Geneticin. This medium was replenished 2–3 times over the following two weeks, after which the plates of cells were fixed (with 10% formalin in phosphate-buffered saline), stained with Coomassie Blue dye, washed in 25% ethanol, and air-dried. During the two weeks of growth, each virus-infected cell gives rise to a colony of Geneticin-resistant cells. Because the LNCX-genome does not encode the functions necessary to produce new virus particles, virus-infected particles do not spread infection to nearby cells. Therefore, all cells not infected during the initial overnight exposure to the virus remain sensitive to the antibiotic, and die during the two week incubation. Consequently, the number of colonies (as visualized by Coomassie blue staining) present at two weeks provides an accurate reflection of the number of infectious virus particles initially applied to the cells. In parallel with all examples shown, control experiments were performed to demonstrate that cells not exposed to virus produced no colonies at two weeks, and cells exposed to untreated virus produced the expected number of colonies.

In order to demonstrate that the conditions necessary for viral inactivation are not exceedingly harmful to the beneficial constituents of proteinaceous products, several experiments were conducted and are reported in Examples 1, 2, 3 and 4 below. Similar conditions were then utilized to inactivate viral particles in the presence of different levels of proteins; these experiments are reported in Examples 5, 6 and 7 below.

Examples of our disclosure are given below to show how variables such as critical fluid type, cosolvent concentration, temperature, pressure and time can effect reduction in viral activity and biological activity. It should be understood that the critical fluid viral inactivation process is not limited to the following examples which are presented to further illustrate the invention.

EXAMPLE 1

Impact of Supercritical Carbon Dioxide and Nitrous Oxide on Bovine Plasma

In order to evaluate if critical, supercritical or near critical fluid treatment would adversely affect the beneficial constituents of plasma, several experiments were carried out with bovine plasma. Aseptically collected bovine blood treated with an anticoagulant (sodium citrate) was centrifuged at a speed of 3,000 rpm for 30 minutes in a refrigerated centrifuge at 10° C. 75ml of the decanted plasma was introduced into the apparatus shown as FIG. 1, contacted with the critical fluid at the conditions listed in the top half of Table 2 and then slowly decompressed to atmospheric conditions.

In this series of experiments, there were two controls— CFI-0 which is the untreated, unprocessed plasma, and CFI-3 which is processed in the critical fluid viral inactivation (CFI) apparatus without critical fluids. The latter control accounts for the mechanical impact of mixing on proteins and other beneficial constituents. The recovered samples were spun down in a refrigerated centrifuge at 3,000 rpm for 30 minutes at 10° C.; the clarified plasma was then sent out to Tufts University Veterinary Diagnostic Laboratory, Boston, Mass. for analysis. The results of this analysis, summarized in the bottom half of Table 1, indicate that supercritical carbon dioxide had an adverse impact on the beneficial constituents of the bovine plasma, namely alkaline phosphatase (AKP), lactic dehydrogenase (LDH) and creatine phosphokinase (CPK), while the impact of supercritical nitrous oxide was much less severe. These adverse effects can be addressed through the use of entrainers and pH controls.

TABLE 2

IMPACT OF CRITICAL FLUID CARBON DIOXIDE AND NITROUS OXIDE ON BOVINE PLASMA

| PARAMETER | CFI-0 | CFI-1 | CFI-2 | CFI-3 |
|---|---|---|---|---|
| Critical Fluid | — | CO2 | N2O | — |
| Pressure (psig) | — | 4,000 | 4,000 | — |

TABLE 2-continued

IMPACT OF CRITICAL FLUID CARBON DIOXIDE AND NITROUS OXIDE ON BOVINE PLASMA

| PARAMETER | CFI-0 | CFI-1 | CFI-2 | CFI-3 |
|---|---|---|---|---|
| Temperature (C.) | 4 | 40 | 40 | 40 |
| Time (mins) | — | 30 | 30 | 30 |
| Glucose (mg/dl) | 64 | 41 | 62 | 60 |
| BUN (mg/dl) | 17 | 17 | 17 | 18 |
| Protein (g/dl) | 6.9 | 5.1 | 6.5 | 6.7 |
| AKP (U/l) | 252 | 0 | 178 | 228 |
| LDH (U/l) | 1,458 | 38 | 1,011 | 1,428 |
| Albumin (g/dl) | 3.4 | 5.5 | 4.2 | 3.2 |
| CPK (U/l) | 547 | 44 | 199 | 432 |

BUN — Blood Urea Nitrogen
LDH — Lactic Dehydrogenase
AKP — Alkaline Phosphatase
CPK — Creatine Phosphokinase

EXAMPLE 2

Impact of Pressure on Critical Fluid Nitrous Oxide on Bovine Plasma

The second set of runs was conducted with supercritical nitrous oxide at different pressures. Within 24 hours after treatment, a SMAC analysis was performed on the recovered plasma by Bioran Laboratories, Cambridge, Mass. All SMAC results were repeated and verified by Bioran Laboratories. The conditions of these runs and the results of the analysis are listed in Table 3. At the end of the experiments, the mixture of critical fluid and bovine plasma was rapidly decompressed (at a rate around 100 psig/sec) and the critical fluid separated from the now treated plasma. The results listed in Table 2 indicate that supercritical nitrous oxide had little or no impact on blood urea nitrogen (BUN), AKP, LDH, albumin, triglycerides and cholesterol over the range of pressures tested, and there was little or no sensitivity to the level of pressure between 1,000 and 3,000 psig. (The glucose values for experiments CFI-4 through CFI-7 are about twice that of the control CFI-00. These results suggest possible disruption of red blood cells which were not removed in the plasma preparation.)

TABLE 3

IMPACT OF PRESSURE ON CRITICAL FLUID NITROUS OXIDE ON BOVINE PLASMA

| PARAMETER | CFI-00 | CFI-4 | CFI-5 | CFI-6 | CFI-7 |
|---|---|---|---|---|---|
| Critical Fluid | — | N2O | N2O | N2O | N2O |
| Pressure (psig) | — | — | 1,000 | 2,000 | 3,000 |
| Temperature (C.) | 4 | 40 | 40 | 40 | 40 |
| Time (mins) | — | 30 | 30 | 30 | 30 |
| Glucose (mg/dl) | 77 | 148 | 149 | 155 | 153 |
| BUN (mg/dl) | 18 | 16 | 15 | 16 | 16 |
| Protein (g/dl) | 7.7 | 6.3 | 5.9 | 6.4 | 6.5 |
| AKP (U/l) | 24 | 30 | 30 | 34 | 35 |
| LDH (U/l) | 1,111 | 891 | 767 | 883 | 891 |
| Albumin (g/dl) | 2.5 | 2.4 | 2.4 | 2.6 | 2.5 |
| Triglycerides (mg/dl) | 11 | 16 | 17 | 18 | 17 |
| Cholesterol (mg/dl) | 143 | 148 | 136 | 150 | 154 |

BUN — Blood Urea Nitrogen
LDH — Lactic Dehydrogenase
AKP — Alkaline Phosphatase
CPK — Creatine Phosphokinase

EXAMPLE 3

Impact of Critical Fluid Type on Bovine Plasma

In this series of experiments, the critical, supercritical or near critical fluid was varied; with the exception of the control—CFI-00—process conditions were 3,000 psig, 40° C. and 30 minutes. The critical fluids tested were nitrous oxide ($N_2O$), ethylene ($C_2H_4$), ethane ($C_2H_6$), propane ($C_3H_8$), tri-fluoromethane ($CHF_3$ or Fr-23), chlorodifluoromethane ($CHClF_2$ or Fr-22). The conditions of these experiments and some relevant thermo-dynamic properties are listed in the top half of Table 4. These solvents, with the exception of propane and Freon-22, are all supercritical at the tested conditions of 3,000 psig and 40° C. The results of explosive decompression experiments with these critical fluids and bovine plasma are listed in the bottom half of Table 4. These results can be compare against values for the control in Table 3. Apart from the doubling of glucose concentration levels and some detrimental effects on LDH in CFI-7 through CFI-12, the first six critical fluids tested in Table 3 had a negligible impact on blood constituents. Near-critical Freon-22 and supercritical Freon-23 had the most significant impact on LDH decreasing concentration by slightly more than 50% of the original value.

TABLE 4

IMPACT OF CRITICAL FLUID TYPE ON BOVINE PLASMA

| PARAMETER | CFI-7 | CFI-8 | CFI-9 | CFI-10 | CFI-11 | CFI-12 | CFI-13 |
|---|---|---|---|---|---|---|---|
| Critical Fluid | N2O | C2H4 | C2H6 | C3H8 | Fr-23 | Fr-22 | N2 |
| Crit. Press. (psia) | 1,051 | 731 | 709 | 616 | 701 | 722 | 493 |
| Crit. Temp. (C.) | 36.4 | 9.2 | 32.2 | 96.6 | 25.9 | 96.0 | −147.0 |
| Pressure (psig) | 3,000 | 3,000 | 3,000 | 3,000 | 3,000 | 3,000 | 3,000 |
| Temperature (C.) | 40 | 40 | 40 | 40 | 40 | 40 | 40 |
| Time (mins) | 30 | 30 | 30 | 30 | 30 | 30 | 30 |
| Glucose (mg/dl) | 153 | 157 | 156 | 161 | 166 | 132 | 68 |
| BUN (mg/dl) | 16 | 17 | 16 | 17 | 16 | 16 | 12 |
| Protein (g/dl) | 6.5 | 6.8 | 6.9 | 7.1 | 6.4 | 6.5 | 6.6 |
| AKP (U/l) | 35 | 34 | 33 | 35 | 26 | 24 | 24 |
| LDH (U/l) | 891 | 808 | 837 | 907 | 522 | 510 | 971 |
| Albumin (g/dl) | 2.5 | 2.7 | 2.5 | 2.6 | 2.7 | 2.8 | 2.3 |
| Triglycerides (mg/dl) | 17 | 19 | 18 | 18 | 30 | 29 | 11 |
| Cholesterol (mg/dl) | 154 | 154 | 152 | 152 | 124 | 134 | 128 |

BUN — Blood Urea Nitrogen
LDH — Lactic Dehydrogenase
AKP — Alkaline Phosphatase
CPK — Creatine Phosphokinase

EXAMPLE 4

Impact of Residence Time and Operating Temperature on the Critical Fluid Treatment of Bovine Plasma The impact of residence time and operating temperature on some of the beneficial constituents of bovine plasma treated by supercritical fluid $N_2O$ at 3,000 psig is listed in Table 5. The data suggests that temperature more than time had an impact on supercritical fluid $N_2O$ treated bovine plasma. For example, both CFI-14 and CFI-15, which were conducted at 30° C., had negligible impacts on glucose, total protein and LDH versus CFI-7, which was conducted at 40° C. Also, there was no significant difference in the impact of CFI-14 and CFI-15, which had residence times of 30 and 5 minutes.

TABLE 5

IMPACT OF RESIDENCE TIME AND OPERATING TEMPERATURE ON THE CRITICAL FLUID TREATMENT OF BOVINE PLASMA

| PARAMETER | CFI-00 | CFI-7 | CFI-14 | CFI-15 |
|---|---|---|---|---|
| Critical Fluid | — | N2O | N2O | N2O |
| Pressure (psig) | — | 3,000 | 3,000 | 3,000 |
| Temperature (C.) | 4 | 40 | 30 | 30 |
| Time (mins) | — | 30 | 30 | 5 |
| Glucose (mg/dl) | 77 | 153 | 74 | 74 |
| BUN (mg/dl) | 18 | 16 | 14 | 17 |
| Protein (g/dl) | 7.7 | 6.5 | 7.3 | 7.2 |
| AKP (U/l) | 24 | 35 | 30 | 29 |
| LDH (U/l) | 1,111 | 891 | 1,018 | 1,057 |
| Albumin (g/dl) | 2.5 | 2.5 | 2.5 | 2.6 |
| Triglycerides (mg/dl) | 11 | 17 | 13 | 10 |
| Cholesterol (mg/dl) | 143 | 154 | 134 | 137 |

BUN — Blood Urea Nitrogen
LDH — Lactic Dehydrogenase
AKP — Alkaline Phosphatase
CPK — Creatine Phosphokinase

EXAMPLE 5

Impact of Residence Time on Critical Fluid Viral Inactivation of Murince-C Retrovirus in Culture Medium Several tests were conducted with 30 ml of culture medium containing murine C-type retroviruses and supercritical nitrous oxide at approximately 3,000 psig and 40° C. These experiments (CFI-18, CFI-19, and CFI-20 listed in Table 6 were conducted at different residence times ranging from 5 to 121 minutes; CFI-21 in Table 6 was conducted with supercritical nitrogen at similar conditions of temperature and pressure for 30 minutes. Between each run, and a described above, the experimental apparatus was rinsed with sterile deionized water, sterilized with 70% ethanol through 7 and 0.5 micron filters, and again rinsed with sterile deionized, distilled water; the apparatus was then dried with filtered compressed nitrogen or air.

After each experiment, the recovered samples were halved; one half was spun down at 2,500 rpm for 10 minutes and the supernatant subjected to 0.45 micron filtration. Titer tests, ability to infect 3T3 fibroblasts and confer G418 resistance, were conducted on duplicate 2.3 ml samples at six different dilutions. The appropriate titers of recovered samples are listed in Table 6. The results indicate that supercritical nitrogen was relatively ineffective in inactivating the retrovirus whereas supercritical nitrous oxide was very effective in inactivating the retrovirus. On the other hand, supercritical nitrous oxide rapidly inactivated the retrovirus in a period between 30 and 121 minutes.

TABLE 6

IMPACT OF RESIDENCE TIME ON CRITICAL FLUID VIRAL INACTIVATION OF MURINE-C RETROVIRUS IN CULTURE MEDIUM

| PARAMETER | Control | CFI-18 | CFI-19 | CFI-20 | CFI-21 |
|---|---|---|---|---|---|
| Critical Fluid | — | N2O | N2O | N2O | N2 |
| Pressure (psig) | — | 2,560 | 2,690 | 3,180 | 3,250 |
| Temperature (C.) | 4 | 43 | 41 | 41 | 41 |
| Time (mins) | — | 30 | 5 | 121 | 30 |
| Titer (cfu/2.3 ml) | 5,000 | 10 | 50 | <5* | 3,000 |
| - log10 Reduction | N/A | 2.7 | 2.0 | >3.0 | 0.2 |

*Detection limit

EXAMPLE 6

Impact of Critical Fluid Type and Cosolvent on the Viral Inactivation of Murine-C Retrovirus in Serum Several critical fluid viral inactivation experiments were conducted with murine-C retrovirus in serum. Proteins are known to have a protective effect on the viability of viruses. These experiments were thus conducted to evaluate the effectiveness of the critical fluid viral inactivation in a protein-rich medium. Murine-C retrovirus in culture medium was mixed 50/50 with serum (serum was a 50/50 mix of Hyclone fetal bovine serum and Hyclone iron supplemented calf serum) and divided into 5 equal aliquots. Experiments were conducted with several critical fluids—nitrous oxide ($N_2O$), nitrous oxide/2 mole % ethanol mixture, chloro-difluoromethane ($CHClF_2$ or Fr-22) and propane ($C_3H_8$) at approximately 3,000 psig and 40° C. for a residence time of 30 minutes. One critical fluid experiment (CFI-26) was conducted at 60° C. These experiments are listed in Table 7. Several controls were conducted on samples which were not treated with critical fluids—one at 40° C., one at 40° C. with 2 mole % ethanol in the serum, and one at 60° C.

Titers were run on controls and recovered samples without polybrene enhancement (in duplicate at six dilutions) and with polybrene enhancement (in duplicate at four dilutions). The titer results indicate that 2 mole % ethanol does not affect the titer but that heating at 60° C. does destroy the retrovirus. The titer results presented in Table 7 are for polybrene enhanced determinations (these valves are consistent with titers determined without polybrene). The 40° C. control had a titer of 65,000 cfu/2.3 ml. The results listed in Table 7 indicate that the presence of protein did reduce the effectiveness of supercritical nitrous oxide by one to two orders of magnitude (compare CFI-27 in Table 6 to CFI-18 in Table 6). Also, 2 mole % ethanol had little or no impact on the effect of supercritical nitrous oxide. Freon-22, however, had a significant impact on murine-C retrovirus, reducing viral activity by some 3.2 log orders of magnitude after 30 minutes of contacting the serum.

TABLE 7

IMPACT OF CRITICAL FLUID TYPE AND COSOLVENT ON THE VIRAL INACTIVATION OF MURINE-C RETROVIRUS IN SERUM

| PARAMETER | Control | CFI-26 | CFI-27 | CFI-28 | CFI-29 | CFI-30 |
|---|---|---|---|---|---|---|
| Critical Fluid | — | N2O | N2O | N2O/EtOH | Fr-22 | C3H8 |
| Pressure (psig) | — | 3,000 | 3,000 | 3,000 | 3,000 | 3,000 |
| Temperature (C.) | 40 | 60 | 40 | 41 | 41 | 41 |

TABLE 7-continued

IMPACT OF CRITICAL FLUID TYPE AND
COSOLVENT ON THE VIRAL INACTIVATION OF
MURINE-C RETROVIRUS IN SERUM

| PARAMETER | Control | CFI-26 | CFI-27 | CFI-28 | CFI-29 | CFI-30 |
|---|---|---|---|---|---|---|
| Time (mins) | — | 30 | 30 | 30 | 30 | 30 |
| Titer (cfu/2.3 ml) | 65,000 | <5* | 3,000 | 5,000 | 40 | 2,500 |
| -log10 Reduction | N/A | >4.1 | 1.4 | 1.1 | 3.2 | 1.4 |

*Detection limit

EXAMPLE 7

Impact of Residence Time, Critical Fluid Type and Pressure on the Viral Inactivation of Murine-C Retrovirus in Serum Based on the results in Example 6, several experiments were conducted with Freon-22 at approximately 3,000 psig and 40° C. to determine the impact of residence time on viral reduction capability. The experiments, listed in Table 8, indicate that Freon-22 can, within the detection limits of the assay, eliminate viral activity within five minutes.

This example also indicates that pressure has a significant impact on the effectiveness of critical fluid viral inactivation. CFI-34 in Table 8 indicate that supercritical nitrous oxide at 5,000 psig and 40° C. for a residence time of 30 minutes inactivated the entire viral population (within the detection limits of the assay), while CFI-27 in Table 8 shows that supercritical nitrous oxide at 3,000 psig and 40° C. for a residence time of 30 minutes reduces virus activity by only 1.4 logs.

TABLE 8

IMPACT OF RESIDENCE TIME, CRITICAL FLUID TYPE AND
PRESSURE ON THE VIRAL INACTIVATION OF MURINE-C
RETROVIRUS IN SERUM

| PARAMETER | Control | CFI-31 | CFI-32 | CFI-33 | CFI-34 | CFI-35 |
|---|---|---|---|---|---|---|
| Critical Fluid | — | Fr-22 | Fr-22 | Fr-22 | N2O | N2 |
| Pressure (psig) | — | 3,000 | 3,000 | 3,000 | 5,000 | 3,000 |
| Temperature (C.) | 40 | 40 | 40 | 41 | 41 | 41 |
| Time (mins) | — | 5 | 15 | 60 | 30 | 60 |
| Titer (cfu/2.0 ml) | 20,000 | <5* | 5 | <5* | <5* | 3,750 3,750 |
| -log10 Reduction | N/A | >3.6 | 3.6 | >3.6 | >3.6 | 0.7 |

*Detection limit

Thus, preferred embodiments of the present invention have been described, which embodiments are capable of further modification and variation by those skilled in the art. Accordingly, it is intended that the examples and the description be intended for illustration purposes only and that the inventions set forth in the claims shall encompass variations and equivalents.

We claim:

1. A method of inactivating one or more virions in a blood derived sample, comprising the steps of:
   (a.) forming an admixture of a blood derived sample with a critical, near critical or supercritical fluid for a time and under conditions effective to unactivate said one or more virions; and,
   (b.) removing the critical, near critical or supercritical fluid to render said one or more virions inactive while retaining the constituents of the one or more inactivated virions to form a processed blood derived product.

2. The method of claim 1 wherein said blood derived sample has one or more proteins which proteins have an activity in said blood derived sample and following removal of said critical, near critical or supercritical fluid retain fifty percent of said activity in the processed blood derived product.

3. The method of claim 1 wherein said blood derived sample exhibits a viral activity and following removal of said critical, near critical or supercritical fluid said processed blood derived product exhibits a four log reduction in viral activity compared to said blood derived sample.

4. The method of claim 1 wherein said critical, supercritical or near critical fluid is at a temperature in the range of 0° C. to 100° C.

5. The method of claim 4 wherein said critical, supercritical or near critical fluid has a temperature that does not exceed 60° C.

6. The method of claim 1 wherein said critical, super critical or near critical fluid has a temperature range of range of 4° C. to 40° C.

7. The method of claim 1 wherein said critical, supercritical or near critical fluid has a pressure in which the admixture is made and maintained which pressure is 0.75 to 20.0 times the critical pressure of the gas comprising such fluid.

8. The method of claim 1 wherein said critical, supercritical or near critical fluid is selected from one or more of the gases of the group consisting of fluorocarbons, chlorofluoromethanes, alkanes, and binary gases.

9. The method of claim 1 wherein said critical, supercritical or near critical fluid is selected from one or more of the gases of the group consisting of nitrous oxide, chlorodifluoromethane, propane and carbon dioxide.

10. The method of claim 1 wherein said critical, supercritical or near critical fluid further comprises one or more modifiers selected from the group consisting of ethanol, methanol, acetone, and ethylene glycol.

11. The method of claim 1 wherein critical, supercritical or near critical fluid is chlorodifluoromethane at approximately 10° C. to 60° C. at 1000 to 4000 psig.

12. The method of claim 1 wherein critical, supercritical or near critical fluid is nitrous oxide at approximately approximately 12° C. to 30° C. at 800 to 1600 psig.

* * * * *